(12) United States Patent
Balda

(10) Patent No.: US 8,989,850 B2
(45) Date of Patent: Mar. 24, 2015

(54) RETRACTABLE MULTI-USE CARDIAC MONITOR

(75) Inventor: Daniel Balda, Indian Harbour Beach, FL (US)

(73) Assignee: Medicomp, Inc., Melbourne, FL (US)

( * ) Notice: Subject to any disclaimer, the term of this patent is extended or adjusted under 35 U.S.C. 154(b) by 817 days.

(21) Appl. No.: 13/111,517

(22) Filed: May 19, 2011

(65) Prior Publication Data

US 2012/0022387 A1    Jan. 26, 2012

Related U.S. Application Data

(60) Provisional application No. 61/347,117, filed on May 21, 2010.

(51) Int. Cl.
| | | |
|---|---|---|
| *A61B 5/0432* | (2006.01) | |
| *A61B 5/0404* | (2006.01) | |
| *A61B 5/0408* | (2006.01) | |
| *A61B 5/00* | (2006.01) | |

(52) U.S. Cl.
CPC ............. *A61B 5/0404* (2013.01); *A61B 5/0408* (2013.01); *A61B 5/0006* (2013.01); *A61B 5/6823* (2013.01); *A61B 5/6826* (2013.01); *A61B 2560/045* (2013.01); *A61B 2562/221* (2013.01)
USPC ......................................... 600/509; 600/523

(58) Field of Classification Search
CPC .. A61B 5/0404; A61B 5/0408; A61B 5/0006; A61B 2562/221; A61B 5/6826; A61B 2560/045; A61B 5/6823
USPC ................... 600/382, 386, 391–392, 509, 523
See application file for complete search history.

(56) References Cited

U.S. PATENT DOCUMENTS

| | | | |
|---|---|---|---|
| 4,606,352 A | | 8/1986 | Geddes et al. |
| 4,858,617 A | * | 8/1989 | Sanders ........................ 600/509 |

(Continued)

FOREIGN PATENT DOCUMENTS

WO    WO 2007/094729 A1    8/2007

OTHER PUBLICATIONS

Puurtinen et al., "Estimation of ECG signal of closely separated bipolar electrodes using thorax models," Proceedings of the 26th Annual International Conference of the IEEE EMBS, San Francisco, California, Sep. 1-5, 2004, 801-804.

*Primary Examiner* — Mark W Bockelman
(74) *Attorney, Agent, or Firm* — Mark R. Malek; William A. Harding; Widerman Malek, PL

(57) ABSTRACT

A retractable multi-use cardiac monitor is provided that includes a memory, and a first side that includes a first housing where a first sensing connector is on the outside of the first housing, and where the first sensing connector is configured to collect electrocardiogram (ECG) data and store ECG data onto the memory. The retractable multi-use cardiac monitor also includes a second housing including a wire retractor and a second sensing connector, where the second sensing connector is on the outside of the second housing, and the wire retractor is configured to extend and retract a wire that connects the second and first sides, and where the second sensing connector is configured to collect ECG data and store ECG data onto the memory. The retractable multi-use cardiac monitor further includes a wireless radio configured to transmit a portion of collected ECG data from the memory to a destination.

2 Claims, 12 Drawing Sheets

(56) References Cited

U.S. PATENT DOCUMENTS

| | | |
|---|---|---|
| 5,813,979 A | 9/1998 | Wolfer et al. |
| 7,554,828 B2 | 6/2009 | Wilson |
| 2002/0045836 A1 | 4/2002 | Alkawwas |
| 2004/0077954 A1 | 4/2004 | Oakley et al. |
| 2005/0049515 A1 | 3/2005 | Misczynski et al. |
| 2008/0097231 A1 | 4/2008 | Balda et al. |
| 2008/0177168 A1* | 7/2008 | Callahan et al. ............... 600/382 |
| 2011/0270100 A1* | 11/2011 | Chang ........................... 600/509 |

* cited by examiner

RETRACTABLE MULTI-USE CARDIAC MONITOR

CROSS REFERENCE TO RELATED APPLICATION

The present application claims the benefit of and priority to U.S. Provisional Patent Application No. 61/347,117, filed May 21, 2010. The foregoing provisional application is incorporated by reference herein in its entirety.

FIELD OF THE INVENTION

The present invention relates generally to the field of cardiac monitoring. Specifically, the present invention is directed towards a retractable multi-use cardiac monitor.

BACKGROUND

The following description of the background of the invention is provided simply as an aid in the understanding of the invention and is not admitted to describe or constitute prior art to the invention.

Cardiac monitoring systems are generally comprised of a series of electrodes attached to the chest area of a patient to collect ECG data. The series of electrodes are usually connected to a series of wires. However, the inventor has perceived that the series of electrodes and interconnected wires are not provided in a compact portable form that allows for easy adjustment of the vector length between the electrodes.

Accordingly, the inventor has perceived that there is a need for a retractable multi-use cardiac monitor that is compact in form and allows for easy adjustment of the vector length between the electrodes of the retractable multi-use cardiac monitor.

SUMMARY

According to one embodiment, a retractable multi-use cardiac monitor is provided. The retractable multi-use cardiac monitor includes a memory, a first side comprising a first housing wherein a first sensing connector is on the outside of the first housing, and wherein the first sensing connector is configured to collect electrocardiogram (ECG) data and store ECG data onto the memory. The retractable multi-use cardiac monitor further includes a second side comprising a second housing including a wire retractor and a second sensing connector, wherein the second sensing connector is on the outside of the second housing, and the wire retractor is configured to extend and retract a wire that connects the second and first sides, and wherein the second sensing connector is configured to collect ECG data and store ECG data onto the memory, and a wireless radio configured to transmit a portion of collected ECG data from the memory to a destination According to another embodiment, a method of collecting electrocardiogram (ECG) data with a retractable multi-use cardiac monitor is provided, wherein the retractable multi-use cardiac monitor includes a memory, a first side that includes a first housing wherein a first sensing connector is on the outside of the first housing, a second side including a second housing and a second sensing connector, wherein the second sensing connector is on the outside of the second housing, and a wireless radio. The method includes collecting ECG data from the first and second sensing connectors of the retractable multi-use cardiac monitor, wherein the first and second sensing connectors are placed against the skin of a chest area of a human patient, recording the collected ECG data onto the memory of the retractable multi-use cardiac monitor, and transmitting a portion of the collected ECG data to a destination.

According to yet another embodiment, a method of determining an optimum electrode vector length between a first sensing connector of a first side of a retractable multi-use cardiac monitor and a second sensing connector of a second side of the retractable multi-use cardiac monitor is provided. The method includes (A) receiving from the retractable multi-use cardiac monitor at a smart phone data representing a distance between the first sensing connector of the retractable multi-use cardiac data monitor and the second sensing connector of the retractable multi-use cardiac data monitor, wherein the smart phone includes a processor, (B) receiving electrocardiogram (ECG) data collected by the retractable multi-use cardiac data monitor through the first and second sensing connectors, (C) recording the ECG data collected in step B and the data representing the distance between the first and second sensing connectors received in step A, and (D) iteratively repeating steps A-C a number of times. The method further includes (E) calculating, by the processor of the smart phone, an optimum electrode vector length between the first sensing connector of the first side of the retractable multi-use cardiac monitor and the second sensing connector of the second side of the retractable multi-use cardiac monitor based on the ECG data collected in step B and the data representing the distance between the first and second sensing connectors received in step A, and (F) generating a notification of that the optimum electrode vector length has been found.

According to yet another embodiment a method of determining an optimum electrode vector length between a first sensing connector of a first side of a retractable multi-use cardiac monitor and a second sensing connector of a second side of the retractable multi-use cardiac monitor is provided. The method includes (A) determining a distance between the first sensing connector of the retractable multi-use cardiac data monitor and the second sensing connector of the retractable multi-use cardiac data monitor, and recording data representing the distance, (B) collecting electrocardiogram (ECG) data through the first and second sensing connectors and recording the collected ECG data, and (C) iteratively repeating A-B a number of times. The method further includes (E) calculating, by a processor of the retractable multi-use cardiac monitor an optimum electrode vector length between the first sensing connector of the first side of the retractable multi-use cardiac monitor and the second sensing connector of the second side of the retractable multi-use cardiac monitor based on the ECG data collected in step B and the data representing the distance between the first and second sensing connectors recorded in step A, and (F) generating a notification of that the optimum electrode vector length has been found.

DETAILED DESCRIPTION

Figure 1:
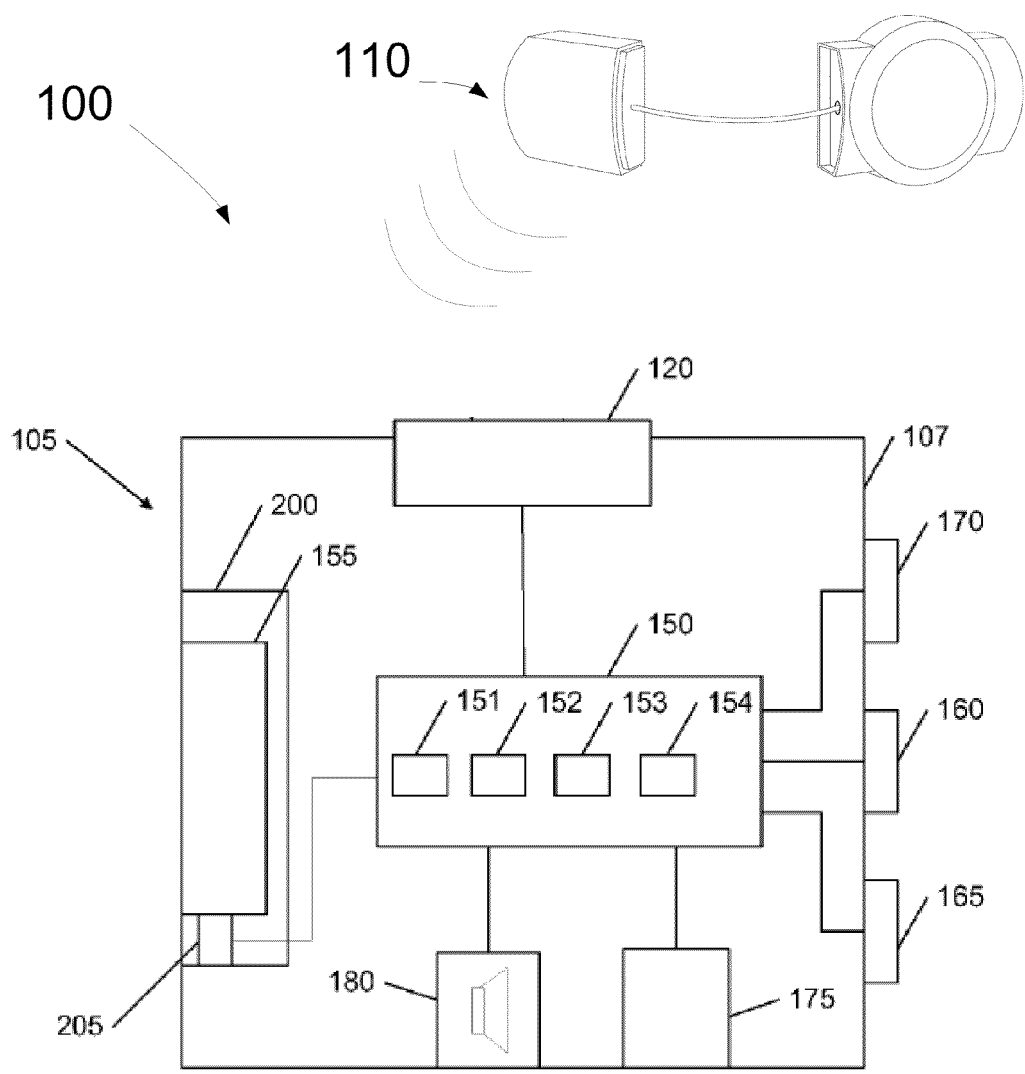
FIG. 1 is an illustration of a cardiac monitor system, according to one embodiment.

Unless otherwise specified, "a" or "an" means "one or more."

With regard to the present disclosure, terms such as "left", "right", and "portion" are used to identify parts of the disclosed retractable multi-use cardiac monitor and are not meant to be limiting, or to mean that such parts of the disclosed retractable multi-use cardiac monitor are in any particular position or orientation relative to the outside environment.

It is to be understood that both the foregoing brief description of the drawings and the following detailed description are exemplary and explanatory only, and are not restrictive of the invention. These and other features, aspects and advantages of the present invention will become apparent from the following description, and the accompanying exemplary embodiments shown in the drawings, which are briefly described below.

Applicant hereby incorporates by reference U.S. Patent Publication No. 2008/0097231, U.S. application Ser. No. 11/550,759, Filed Oct. 18, 2006, and published Apr. 28, 2008. For example, the retractable multi-use cardiac monitor 110 as herein described may be used as a wearable electrode system (110 of U.S. Patent Publication No. 2008/0097231) within a cardiac event monitoring system (100 of U.S. Patent Publication No. 2008/0097231).

Cardiac event monitoring is a procedure that is conducted on patients who report symptoms that may be cardiac in origin, and that occur infrequently, such as, for example, three times or less in one week. Cardiac monitoring is performed by the sensing and storage of electrocardiogram (ECG) data that characterizes activity of a patient's heart by a "cardiac monitor." In some instances, "event monitoring" is used to detect clinically significant heart related events. Event monitoring may be performed by patient activation, whereby the patient senses a cardiac event and causes data to be recorded. In other embodiments of event monitoring, a cardiac monitor analyzes incoming ECG data, identifies a clinically significant ECG event, and stores data related to the detected ECG event (e.g. an event monitor may identify particular types of Arrhythmias). In some embodiments, the cardiac monitor's ability to analyze incoming ECG data allows the cardiac monitor to detect a cardiac condition where a patient is otherwise asymptomatic. Another type of monitoring is "Holter" monitoring. Holter monitoring is directed to constant recording and storage of ECG data from a patient. The quality and amount of ECG data recorded and stored varies based on quality requirements and memory storage limitations. Another cardiac monitoring technology is mobile cardiac telemetry. Mobile cardiac telemetry cardiac monitors may be configured to perform various types of event monitoring as well as constant storage of ECG similar to a holter monitor. In some embodiments, mobile cardiac telemetry monitors operate using auto-push technology that is configured to automatically transmit collected data to a monitoring center. A patient generally carries a cardiac monitor during a testing period, which can last for several days or up to, for example, 30 days.

FIG. 1 illustrates an example of a cardiac monitor system. Referring to FIG. 1, a cardiac monitor system 100 includes a base unit 105 (the cardiac monitor of the illustrated system of FIG. 1), and a retractable multi-use cardiac monitor 110. The retractable multi-use cardiac monitor 110 may include a processor and a memory. The processor may be a microcontroller or a microprocessor. The memory may be a RAM, EEPROM, FLASH, or any other suitable volatile or non-volatile storage medium or device. The base unit 105 includes a base connector 120 and a body 107 that houses the electrical components and includes a user interface. The retractable multi-use cardiac monitor 110 collects ECG data from a patient and provides that data to the base unit 105 through wireless communication by a wireless radio. In some embodiments, the retractable multi-use cardiac monitor 110 stores the collected ECG data in a memory of the retractable multi-use cardiac monitor 110 prior to transmission. The wireless communication between the retractable multi-use cardiac monitor 110 and the base unit 105 may be accomplished using any one of a variety of different wireless technologies including but not limited to 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In an alternative embodiment, the communication between the retractable multi-use cardiac monitor 110 and the base unit 105 may be wired. Further, in some embodiments the retractable multi-use cardiac monitor 110 is powered by a battery, while in other embodiments the retractable multi-use cardiac monitor 110 is powered by a wired connection to base unit 105. In yet further embodiments, the retractable multi-use cardiac monitor 110 collects other biological data, such as temperature, and provides such data to base unit 105 by a wireless radio or through a wired connection as discussed above which may be further transmitted as discussed in reference to FIG. 2C or viewed by a health care professional as discussed below.

Figure 2A:
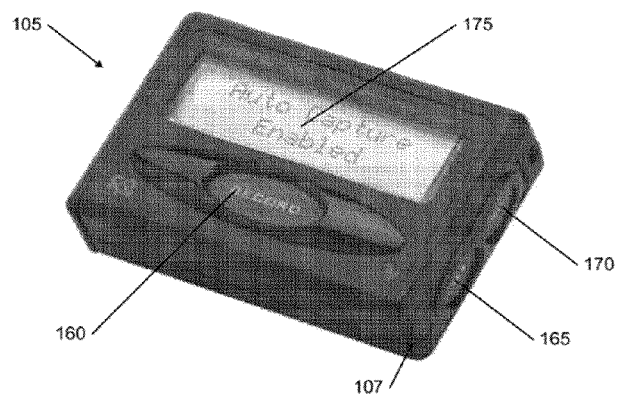
FIG. 2A is an illustration of a cardiac monitor system, according to one embodiment.
Figure 2B:
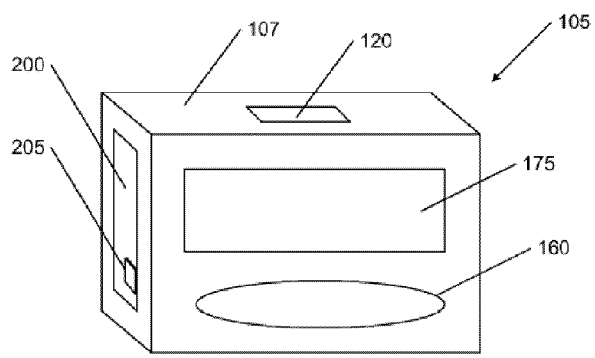
FIG. 2B is an illustration of a cardiac monitor system, according to one embodiment.

Referring now to FIGS. 1, 2A and 2B, the base unit 105 is pager-sized, and is either handheld or patient-worn. The base unit 105 includes the body 107 that houses components that control operation of the cardiac monitor system 100. Thus, the base unit 105 includes a controller 150 within the body 107, and various input and output devices coupled to the controller 150 through the body 107. The controller 150 receives power from a power source 155 that may be provided by batteries that are placed within a compartment 200 on a side of the body 107. The body 107 and the battery compartment 200 can be made of a suitable non-conductive lightweight material, such as a rigid plastic. The power source 155 may be turned off and on by a switch 205 (FIGS. 1 and 2B) accessible on the compartment 200 and connected to the power source 155 and the controller 150.

The controller 150 includes a processor 151, memory 152, a clock 153, and a counter 154 to process signals from the retractable multi-use cardiac monitor 110, receive input from a patient or a service technician using the system 100, and transmit recorded data to a monitoring center, as provided by a health professional, a clinic, or a hospital. In an alternative embodiment, input received from the retractable multi-use cardiac monitor 110 is retained by the base unit 105 and displayed on the base unit 105 at a later time. For example, the input received from the retractable multi-use cardiac monitor 110 may later be shown to a doctor or other health professional during a patient visit. In some embodiments, the base unit 105 both transmits collected data to a monitoring center and retains collected data for later display or use.

The input devices on the base unit 105 include a symptom record button 160, a yes/transmit button 165, and a no button 170. The yes/transmit button 165 can be used in one of two ways: it can be used as a response button to answer "yes" when queried by the controller 150, or it can be used to indicate to the controller 150 to transmit the ECG. The no button 170 can be used in one of two ways: it can be used as a response button to answer "no" when queried by the controller 150, it can be used to indicate to the controller 150 to cancel a transmission of an ECG.

The output devices on the base unit 105 include a display 175 such as a liquid crystal display (LCD) that provides an interface with the patient and/or a technician, and a speaker 180 for transmitting data regarding the recording. For example, the display 175 may be used to show data collected from the retractable multi-use cardiac monitor 110 to a health care professional during a patient visit.

The system 100 can be worn for days or weeks, as it is intended for use by patients who are experiencing symptoms that are transient and infrequent in nature. The base unit 105 can be worn outside the patient's clothing if there is any chance that moisture (for example, sweat) might come in contact with the base unit 105. The base unit 105 can be worn under outer wear, such as raincoats or jackets, for protection during wet or cold conditions. In one embodiment, the base unit 105 may operate as a Holter monitor, or may operate as an event monitor. In an alternative embodiment the base unit 105 may operate as a mobile cardiac telemetry monitor. In some embodiments, the base unit 105 may operate as both a Holter monitor and an event monitor.

Figure 2C:
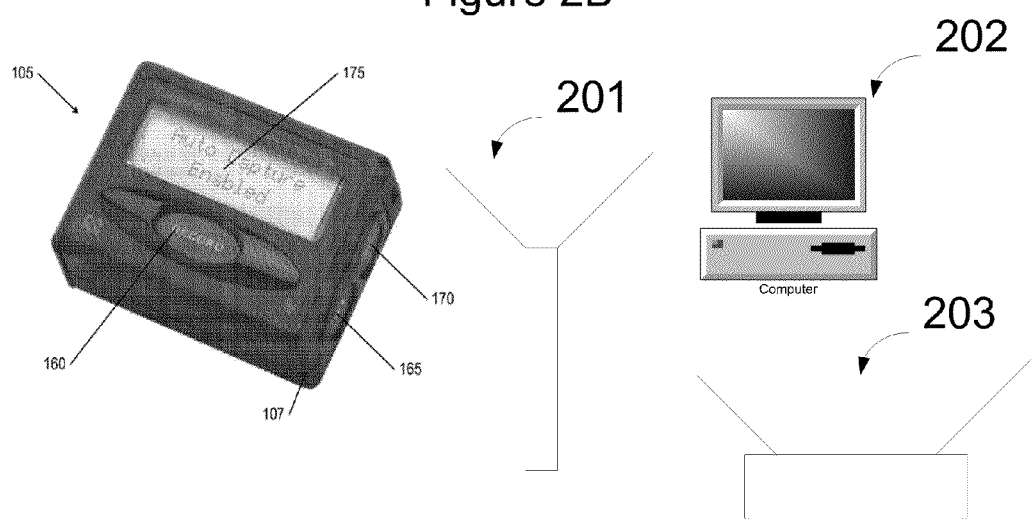
FIG. 2C is an illustration of a cardiac monitor system, according to one embodiment.

FIG. 2C illustrates various communication schemes for the base unit 105. In some embodiments, the base unit 105 may transmit data to a monitoring center, as provided by a health professional, a clinic, or a hospital by communicating with a cellular tower 201 of a cellular network. In an alternative embodiment, the base unit 105 may transmit data to a monitoring center by communicating with a computer 202 that includes an application which stores and forwards the data to the monitoring center through the Internet (e.g. by email). The application on computer 202 may also be configured to allow a user of the base unit 105 to print reports of the data collected by the base unit 105. Communication with the computer 202 may be wired or wireless. For example, the base unit 105 may plug into the computer 202 using a USB or firewire cable. In an alternative embodiment, the base unit 105 may communicate with the computer 202 through a variety of different wireless technologies including but not limited to 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In another embodiment, the base unit 105 simply communicates with a wireless router 203 which then communicates to the monitoring center through the Internet. The wireless router 203 may support any number of wireless technologies including but not limited to IEEE 802.11 (Wi-Fi). In a related embodiment, the base unit 105 is configured to detect the presence of the wireless router 203, and when the presence of the wireless router 203 is detected, the base unit 105 opportunistically transmits collected data to the wireless router 203 which then transmits the data to the monitoring center. In yet another embodiment, the base unit 105 is configured to transmit data to a monitoring center over a telephone connection by audio modulation through the speaker 180. In yet further embodiments, the base unit 105 transmits collected data to the monitoring center through any number of intermediaries and through any number of communication technologies.

Figure 3A:
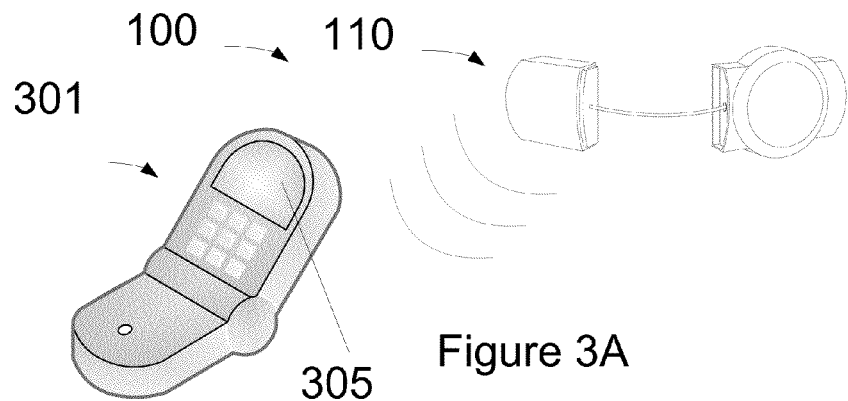
FIG. 3A is an illustration of a cardiac monitor system, according to one embodiment.

FIG. 3A illustrates an alternative embodiment where a cardiac monitoring system 100 is comprised of a smart phone 301 (the cardiac monitor of the illustrated system of FIG. 3A) as well as a retractable multi-use cardiac monitor 110. The smart phone 301 may include a processor and a memory (not illustrated as they are within the smart phone 301). The smart phone 301 also includes a display screen 305. In the disclosed embodiment, the retractable multi-use cardiac monitor 110 transmits collected ECG data to the smart phone 301. In some embodiments, the retractable multi-use cardiac monitor 110 stores the collected ECG data in a memory of the retractable multi-use cardiac monitor 110 prior to transmission. The smart phone 301 may operate as a Holter monitor, or may operate as an event monitor. In an alternative embodiment the smart phone 301 may operate as a mobile cardiac telemetry monitor. In some embodiments, the smart phone 301 may operate as both a Holter monitor and an event monitor. In one embodiment, the retractable multi-use cardiac monitor 110 wirelessly transmits collected ECG data to the smart phone 301 by a wireless radio. The wireless communication between the retractable multi-use cardiac monitor 110 and the smart phone 301 may be accomplished using any one of a variety of different wireless technologies including but not limited to 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In an alternative embodiment, the communication between the retractable multi-use cardiac monitor 110 and the smart phone 301 may be wired. Further, in some embodiments the retractable multi-use cardiac monitor 110 is powered by a battery, while in other embodiments the retractable multi-use cardiac monitor 110 is powered by a wired connection to smart phone 301. As noted above, the retractable multi-use cardiac monitor 110 may include a processor and a memory. The processor may be a microcontroller or a microprocessor. The memory may be a RAM, EEPROM, FLASH, or any other suitable volatile or non-volatile storage medium or device. In yet further embodiments, the retractable multi-use cardiac monitor 110 collects other biological data, such as temperature, and provides such data to smart phone 301 by a wireless radio or through a wired connection as discussed above which may be further transmitted as discussed in reference to FIG. 3B or viewed by a health care professional as discussed below.

The smart phone 301 may be configured to transmit data to a monitoring center, as provided by a health professional, a clinic, or a hospital. In an alternative embodiment, input received from the retractable multi-use cardiac monitor 110 is retained by the smart phone 301 and displayed on the smart phone 301 at a later time or used at a later time. For example, the input received from the retractable multi-use cardiac monitor 110 may later be shown to a doctor or other health professional during a patient visit on the display screen 305 of the smart phone 301. In some embodiments, the smart phone 301 both transmits collected data to a monitoring center and retains collected data for later display or use.

Figure 3B:
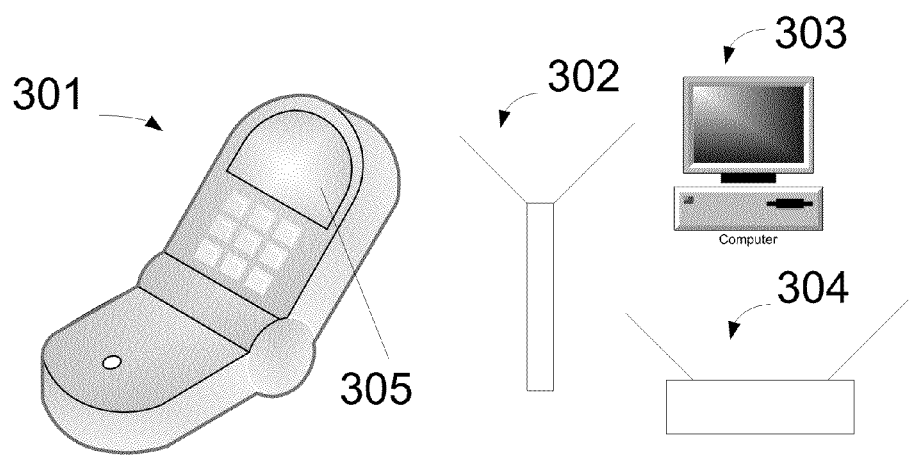
FIG. 3B is an illustration of a cardiac monitor system, according to one embodiment.

FIG. 3B illustrates various communication schemes for the smart phone 301. In some embodiments, the smart phone 301 may transmit data collected from the retractable multi-use cardiac monitor 110 to a monitoring center, as provided by a health professional, a clinic, or a hospital by communicating with a cellular tower 302 of a cellular network. In an alternative embodiment, the smart phone 301 may transmit data to a monitoring center by communicating with a computer 303 that includes an application which stores and forwards the data to the monitoring center through the Internet (e.g. by email). The application on computer 303 may also be configured to allow a user of the smart phone 301 to print reports of the ECG data collected by the smart phone 301. Communication with the computer 302 may be wired or wireless. For example, the smart phone 301 may plug into the computer using a USB or firewire cable. In an alternative embodiment, the smart phone 301 may communicate with the computer 303 through a variety of different wireless technologies including but not limited to 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In another embodiment, the smart phone 301 simply transmits collected data to a wireless router 304 which then transmits the data to the monitoring center through the Internet. The wireless router 304 may support any number of wireless technologies including but not limited to IEEE 802.11 (Wi-Fi). In a related embodiment, the smart phone 301 is configured to detect the presence of the wireless router 304, and when the presence of the wireless router 304 is detected, the smart phone 301 opportunistically transmits collected data to the wireless router 304 which then transmits the data to the monitoring center. In yet another embodiment, the smart phone 301 is configured to transmit data to a monitoring center over a telephone connection by audio modulation. In yet further embodiments, the smart phone 301 transmits collected data to the monitoring center through any number of intermediaries and through any number of communication technologies.

Regarding the transmission of data, the retractable multi-use cardiac monitor 110 may store collected data on an on-board memory and "push" the data to a cardiac monitor (e.g. base unit 105 of FIG. 1 or smart phone 301 of FIG. 3A). Alternatively, the retractable multi-use cardiac monitor 110 may store collected data on an on-board memory and is designed to await a request from a cardiac monitor (e.g. base unit 105 of FIG. 1 or smart phone 301 of FIG. 3A) to "pull" data from the retractable multi-use cardiac monitor 110. Further, the retractable multi-use cardiac monitor 110 may be configured to stream data as it is collected directly to a cardiac monitor (e.g. base unit 105 of FIG. 1 or smart phone 301 of FIG. 3A).

Figure 3C:
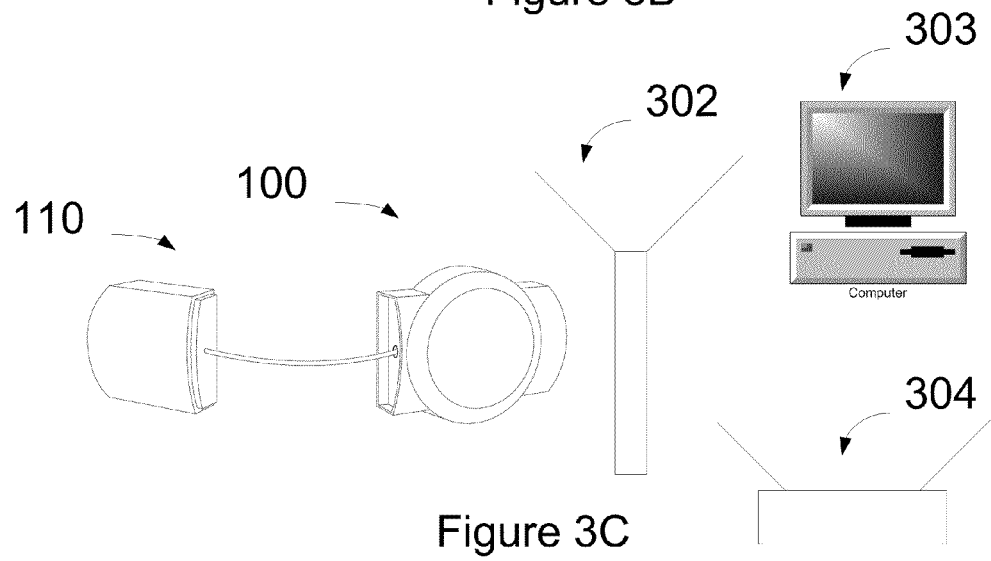
FIG. 3C is an illustration of a cardiac monitor system, according to one embodiment.

FIG. 3C illustrates an embodiment where the multi-use cardiac monitor 110 itself comprises the entire cardiac monitoring system 100. The multi-use cardiac monitor 110 may operate as a Holter monitor, or may operate as an event monitor. In an alternative embodiment the multi-use cardiac monitor 110 may operate as a mobile cardiac telemetry monitor. In some embodiments, the multi-use cardiac monitor 110 may operate as both a Holter monitor and an event monitor. In some embodiments, the multi-use cardiac monitor 110 is configured to transmit collected ECG data to a monitoring center, as provided by a health professional, a clinic, or a hospital. In some embodiments, the retractable multi-use cardiac monitor 110 stores the collected ECG data in a memory of the retractable multi-use cardiac monitor 110 prior to transmission. In an alternative embodiment, the retractable multi-use cardiac monitor 110 includes a display screen and the retractable multi-use cardiac monitor 110 retains any collected ECG data and displays the collected ECG data at a later time. For example, the collected ECG data may later be shown to a doctor or other health professional during a patient visit on a display screen (e.g., 2101 or FIG. 21 or 2201 of FIG. 22) of the retractable multi-use cardiac monitor 110. In some embodiments, the retractable multi-use cardiac monitor 110 both transmits collected ECG data to a monitoring center and retains collected ECG data for later display. As noted above, the retractable multi-use cardiac monitor 110 may include a processor and a memory. The processor may be a microcontroller or a microprocessor. The memory may be a RAM, EEPROM, FLASH, or any other suitable volatile or non-volatile storage medium or device. In yet further embodiments, the retractable multi-use cardiac monitor 110 collects other biological data, such as temperature, and transmits such data as discussed above and below, and may retain the data for later display or use.

FIG. 3C also illustrates various communication schemes for the retractable multi-use cardiac monitor 110 where it comprises the entire cardiac monitor system 100. In some embodiments, the retractable multi-use cardiac monitor 110 may transmit collected data to a monitoring center, as provided by a health professional, a clinic, or a hospital by communicating with a cellular tower 302 of a cellular network by a wireless radio. In an alternative embodiment, the retractable multi-use cardiac monitor 110 may transmit data to a monitoring center by communicating with a computer 303 that includes an application which stores and forwards the data to the monitoring center through the Internet (e.g. by email). The application on computer 303 may also be configured to allow a user of the retractable multi-use cardiac monitor 110 to print reports of the data collected by the retractable multi-use cardiac monitor 110. Communication with the computer 302 may be wired or wireless by a wireless radio. For example, the retractable multi-use cardiac monitor 110 may plug into the computer using a USB or firewire cable. In an alternative embodiment, the retractable multi-use cardiac monitor 110 may communicate with the computer 303 through a variety of different wireless technologies including but not limited to 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In another embodiment, the retractable multi-use cardiac monitor 110 by a wireless radio simply transmits collected data to a wireless router 304 which then transmits the data to the monitoring center through the Internet. The wireless router 304 may support any number of wireless technologies including but not limited to IEEE 802.11 (Wi-Fi). In a related embodiment, the retractable multi-use cardiac monitor 110 is configured to detect the presence of the wireless router 304, and when the presence of the wireless router 304 is detected, the retractable multi-use cardiac monitor 110 opportunistically transmits collected data by a wireless radio to the wireless router 304 which then transmits the data to the monitoring center. In yet another embodiment, the retractable multi-use cardiac monitor 110 is configured to transmit data to a monitoring center over a telephone connection by audio modulation. In yet further embodiments, the retractable multi-use cardiac monitor 110 transmits collected data to the monitoring center through any number of intermediaries and through any number of communication technologies.

Figure 4:
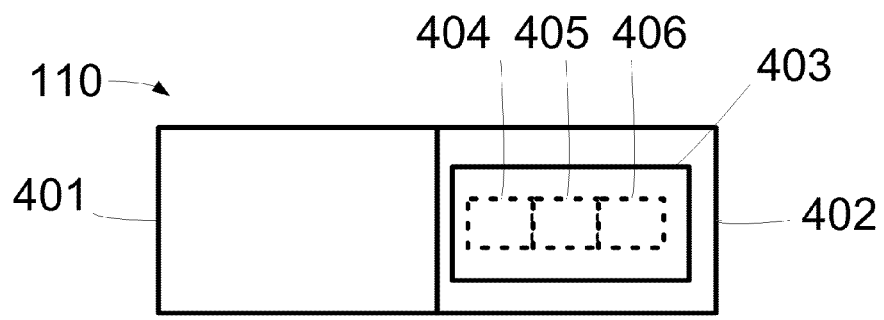
FIG. 4 is a top-down view of a retractable multi-use cardiac monitor, according to one embodiment.

FIG. 4 is a top-down view of a retractable multi-use cardiac monitor 110, according to one embodiment. The retractable multi-use cardiac monitor 110 includes left 401 and right sides 402 each comprised of a left and right side housing (also referenced as 401 and 402 respectively). The retractable multi-use cardiac monitor 110 may be comprised of any one of a number of different materials, including but not limited to plastic and metal. The illustrated embodiment of FIG. 1 includes a symptom button 403 on the right 402 side of the retractable multi-use cardiac monitor 110. In one embodiment, the symptom button 403 may be used by the patient to "wake up" the cardiac monitor with which the retractable multi-use cardiac monitor 110 is associated, such that the cardiac monitor may begin recording data as either a Holter or event or MCT monitor depending on the cardiac monitor's configuration. In an alternative embodiment, the symptom button 403 is used to indicate that a cardiac "event" has occurred, and the retractable multi-use cardiac monitor 110 may begin to record data relative to the "event." In various alternative embodiments, the symptom button 403 may be used as an input to the retractable multi-use cardiac monitor 110, a cardiac monitor with which the retractable multi-use cardiac monitor 110 is associated, or any other portion of a system with which the retractable multi-use cardiac monitor 110 is associated. In an alternative embodiment, the symptom button 403 may be disposed on the left 401 side of the retractable multi-use cardiac monitor 110. The embodiment of FIG. 4 also illustrates each of a processor 404, a memory 405, and a wireless radio 406. Each of processor 404, a memory 405, and a wireless radio 406 are illustrated with dashed lines because they lie below the outer surface of the right side housing 402 and within the right side housing 402. One of skill in the art would appreciate that each of the processor 404, memory 405, and wireless radio 406 may be placed in various locations within the retractable multi-use cardiac monitor 110. For example, processor 404 could be included in the left side housing 401. As noted above, each of the processor 404, memory 405, and wireless radio 406 may be of various types in various embodiments.

Figure 5:
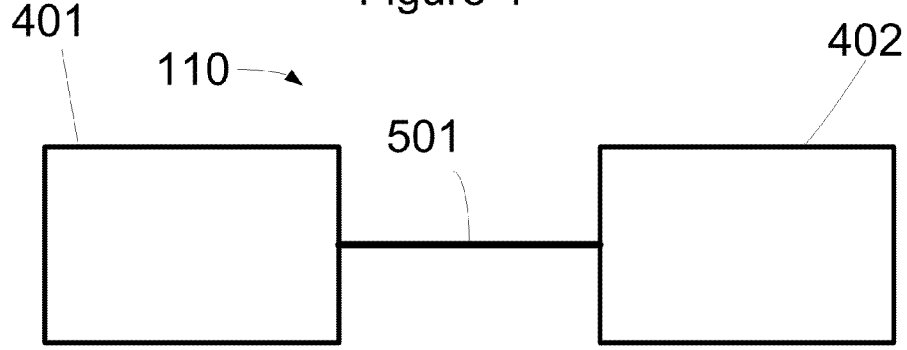
FIG. 5 is a top-down view of a retractable multi-use cardiac monitor, according to one embodiment.

FIG. 5 is also a top-down view of a retractable multi-use cardiac monitor 110, according to one embodiment. The embodiment of FIG. 5 illustrates a retractable wire 501 that connects the left 401 and right 402 sides of the retractable multi-use cardiac monitor 110. The wire 501 may be fiber-optic or electrical. Further, the wire 501 may be shielded or non-shielded. In one embodiment, the wire 501 retracts into the right side 402. In another embodiment, the wire 501 retracts into the left side 401. In both embodiments, the left 401 and right 402 sides of retractable multi-use cardiac monitor 110 may be extended away from and toward one another. The retractable nature of the retractable multi-use cardiac monitor 110 allows for easy and convenient storage of the wire 501.

Figure 6:
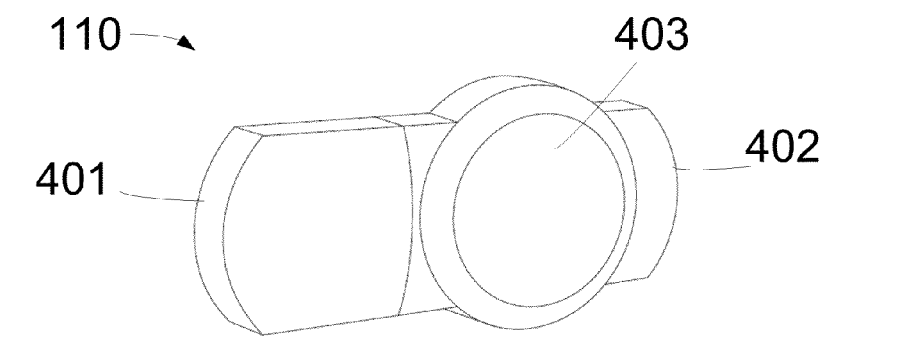
FIG. 6 is a top-down view of a retractable multi-use cardiac monitor, according to one embodiment.
Figure 6:
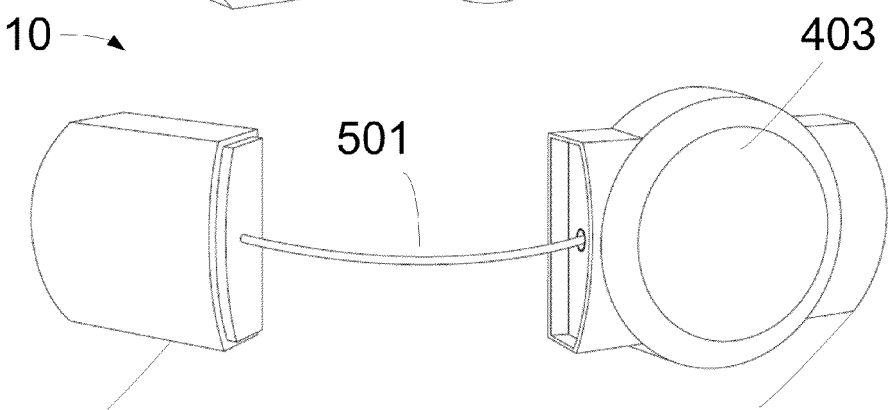

FIG. 6 is yet another illustration of an embodiment of a retractable multi-use cardiac monitor 110. The illustrated embodiment includes left 401 and right 402 sides, as well as a retractable wire 501. The illustrated embodiment also includes a symptom button 403 on the right side 402 of the retractable multi-use cardiac monitor 110.

Figure 7:
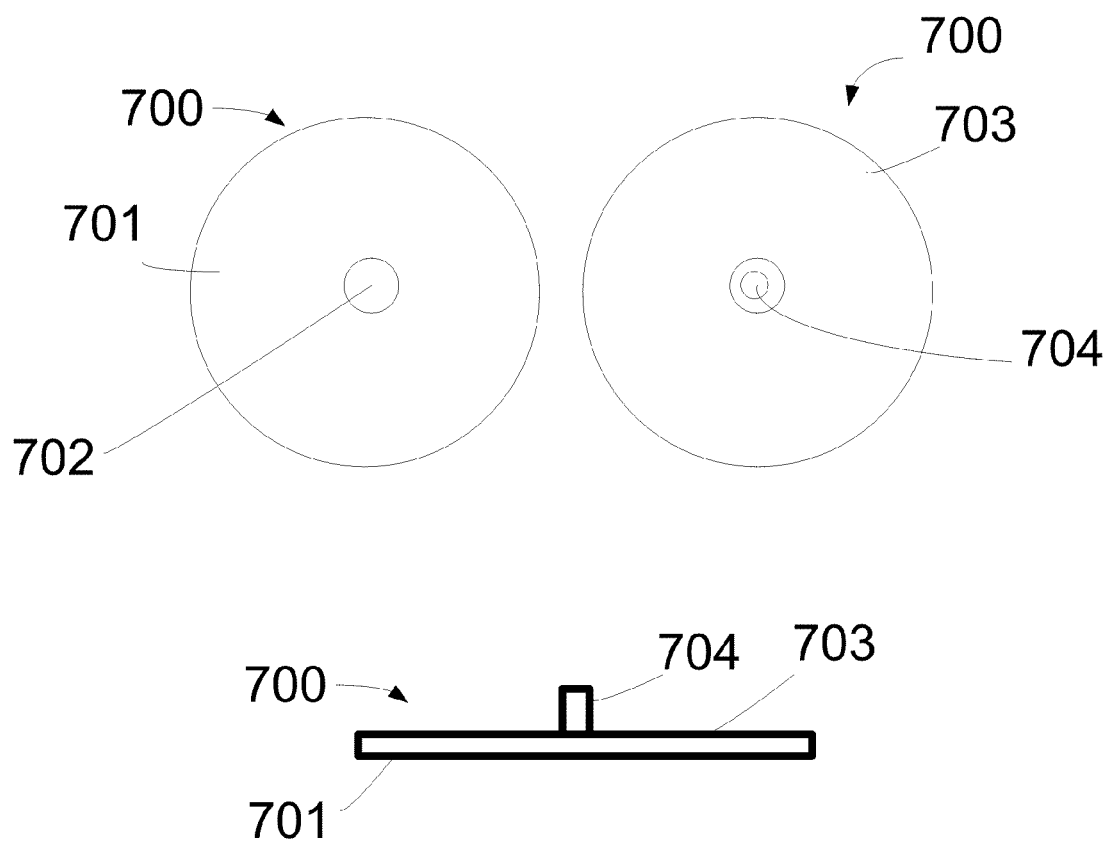
FIG. 7 is an illustration of a wearable electrode, according to one embodiment.

FIG. 7 is a top-down view of a wearable electrode 700, according to one embodiment. The wearable electrode 700 is comprised of an electrode contact 702 that is configured to contact skin. The wearable electrode 700 can detect electrical signals from a patient's heart through the electrode contact 702. The wearable electrode 700 also includes a top surface 703, as well as a bottom surface 701 that may include adhesive to facilitate connection of the wearable electrode 700 to the skin. The wearable electrode 700 also includes a connector 704 to allow the wearable electrode to be connected to a device. The connector 704 is illustrated as a metal post. In some embodiments, the bottom surface 701 is also coated with a gel that improves electrical conduction between the patient's skin and the electrode contact 702.

Figure 8:
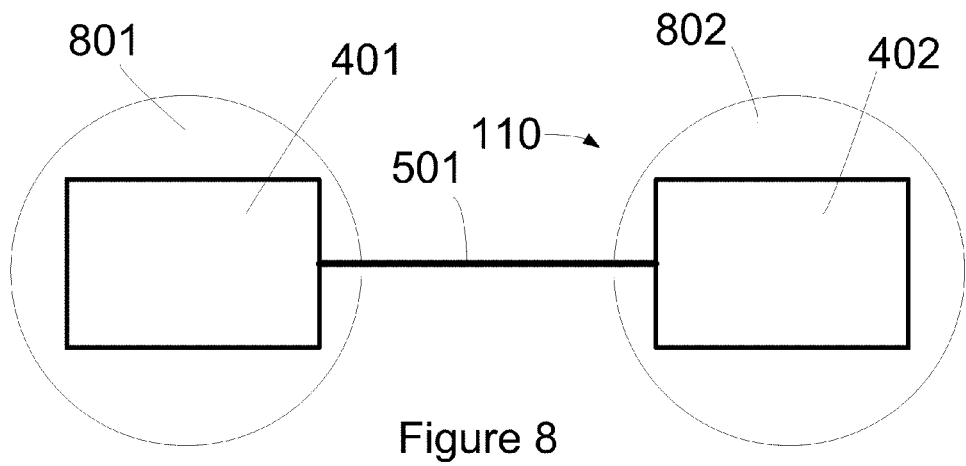
FIG. 8 is a top-down view of a retractable multi-use cardiac monitor with wearable electrodes attached, according to one embodiment.
Figure 9:
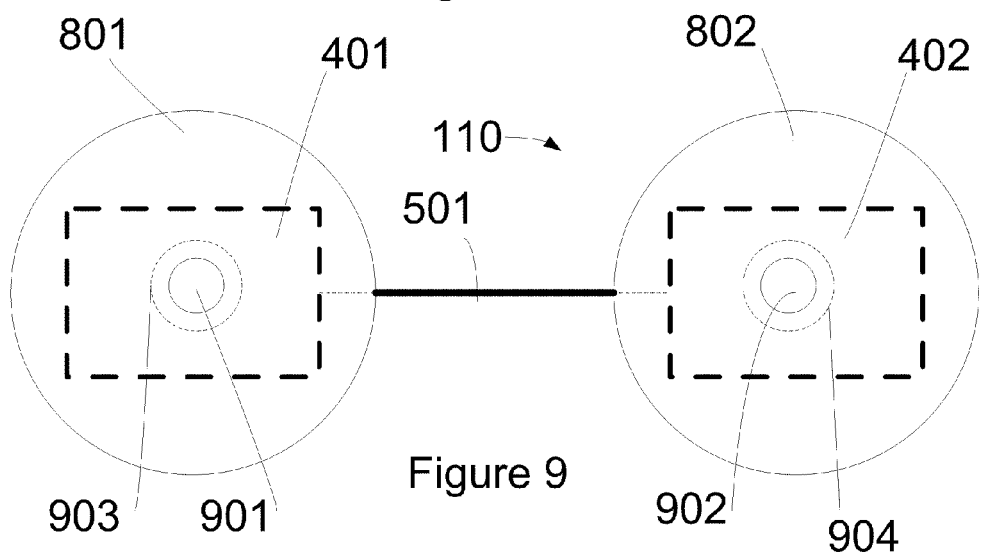
FIG. 9 is a bottom-up view of a retractable multi-use cardiac monitor with wearable electrodes attached, according to one embodiment.

FIG. 8 is a top-down view of a retractable multi-use cardiac monitor 110 with wearable electrodes (left 801 and right 802) attached, according to one embodiment. FIG. 9 is a bottom-up view of a retractable multi-use cardiac monitor 110 with wearable electrodes (left 801 and right 802) attached, according to one embodiment. The left wearable electrode 801 includes a left electrode contact 901 and the right wearable electrode 802 includes a right electrode contact 902. The left 801 and right 802 wearable electrodes connect to the left 401 and right 402 sides of the retractable multi-use cardiac monitor 110 by connection to the left 903 and right 904 sensing connectors. By way of example, FIG. 7 illustrates a connector 704 for a wearable electrode 700. In one embodiment, the sensing connectors (903 and 904) may be configured to accept the connector post 704 for connection to a wearable electrode.

As discussed above with respect to FIG. 7, these wearable electrodes may be configured to contact the skin of a patient to detect electrical signals of the patient's heart through the electrode contacts. In one embodiment, the wearable electrodes (left 801 and right 802) and consequently the electrode contacts (left 901 and right 902) are designed to be temporarily placed against the patient's skin by the patient to detect a small amount of ECG data. For example, a patient may not be feeling well, and may desire to make a short recording of ECG data by holding the wearable electrodes (left 801 and right 802) of the retractable multi-use cardiac monitor 110 against their skin for short period. In another embodiment, the wearable electrodes (left 801 and right 802) and consequently the electrode contacts (left 901 and right 902) are designed to be attached for an extended period of time. As discussed above, in some embodiments an adhesive is provided for wearable electrodes, which facilitates the attachment of the left 801 and right 802 wearable electrodes for an extended period of time. The left 401 and right 402 sides of the retractable multi-use cardiac monitor 110 are shown as dashed lines in this bottom-up view because they are disposed behind the left 801 and right 802 wearable electrodes. Similarly, the left 903 and right 904 sensing connectors are shown as dashed lines in this bottom-up view because they are disposed behind the left 801 and right 802 wearable electrodes. The left 903 and right 904 sensing connectors, or the combination of the left 801 and right 802 wearable electrodes with the left 903 and right 904 sensing connectors collect ECG and other biological data.

Figure 10:
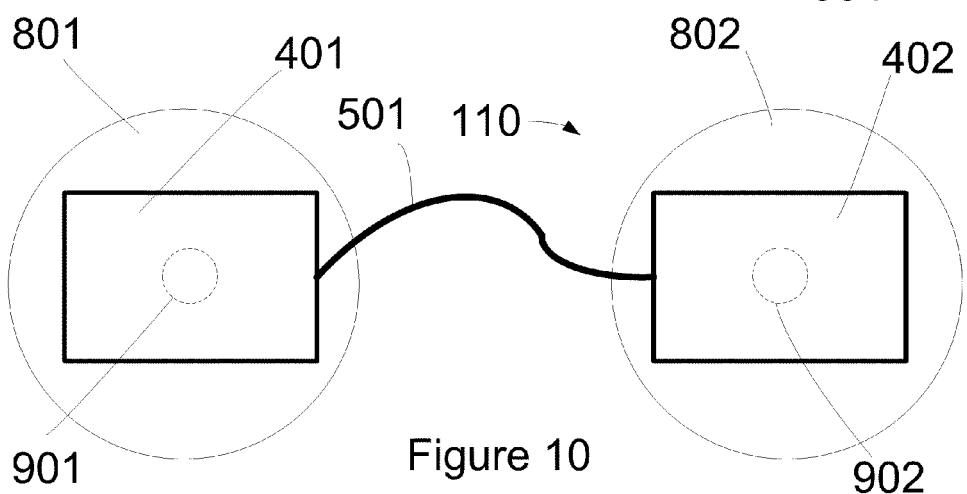
FIG. 10 is a top-down view of a retractable multi-use cardiac monitor with wearable electrodes attached, according to one embodiment.

FIG. 10 is a top-down view of a retractable multi-use cardiac monitor with wearable electrodes (left 801 and right 802) attached. The FIG. 10 embodiment illustrates that the wire 501 may be flexible, and may move flexibly in any direction. FIG. 10 illustrates the left 901 and right 902 electrode contacts as dashed lines in this top-down view because they are disposed behind the left 401 and right 402 sides, as well as the left 801 and right 802 wearable electrodes, respectively.

Figure 11:
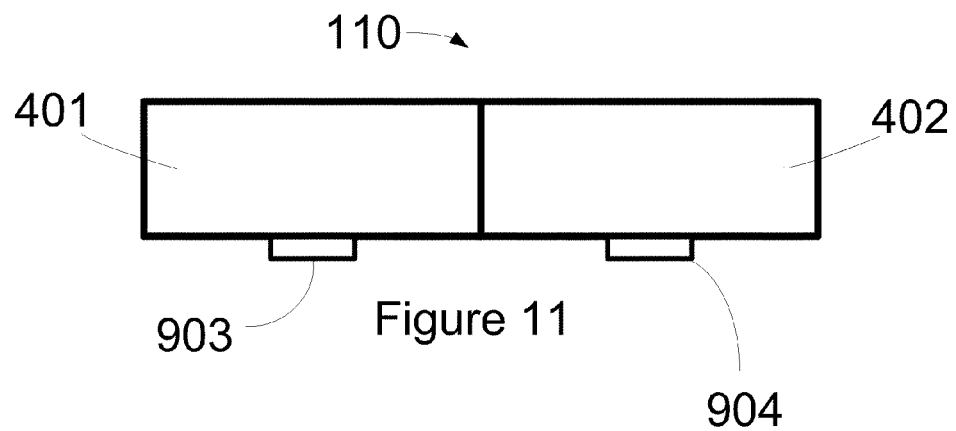
FIG. 11 is a side-view of a retractable multi-use cardiac monitor, according to one embodiment.

FIG. 11 is a side-view of a retractable multi-use cardiac monitor 110, according to one embodiment. FIG. 11 illustrates left 903 and right 904 sensing connectors which protrude away from the left 401 and right 402 sides of the retractable multi-use cardiac monitor 110.

Figure 12:
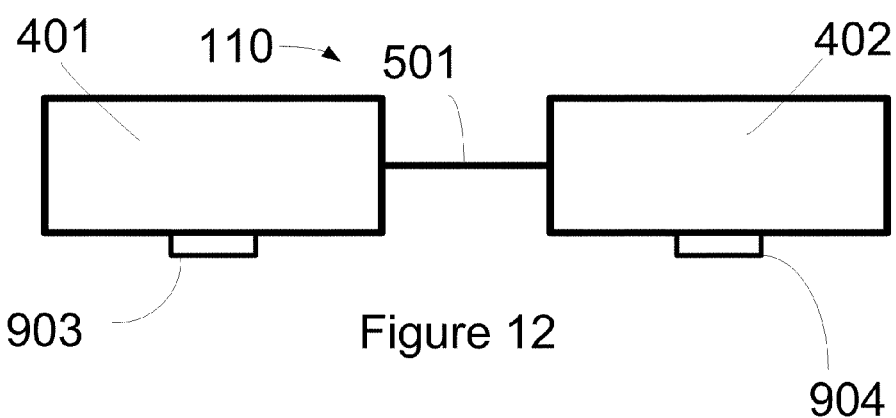
FIG. 12 is a side-view of a retractable multi-use cardiac monitor, according to one embodiment.
Figure 13:
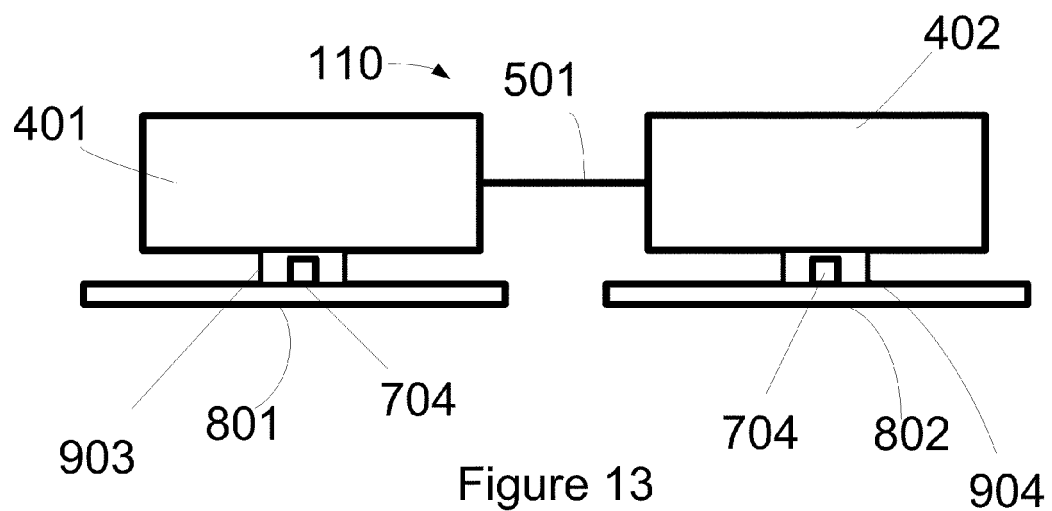
FIG. 13 is a side-view of a retractable multi-use cardiac monitor with wearable electrodes attached, according to one embodiment.

FIG. 12 is a side-view of a retractable multi-use cardiac monitor 110, according to one embodiment. FIG. 12 illustrates the extractable wire 501 that connects the left 401 and right 402 sides of the retractable multi-use cardiac monitor 110. FIG. 13 is a side-view of a retractable multi-use cardiac monitor 110 with wearable electrodes (left 801 and right 802) attached, according to one embodiment. FIG. 13 similarly illustrates the extractable wire 501 that connects the left 401 and right 402 sides of the retractable multi-use cardiac monitor 110. FIG. 13 also illustrates an embodiment in which the sensing connectors 903 and 904 are configured to accept a connector post 704 for wearable electrodes 801 and 802.

Figure 14A:
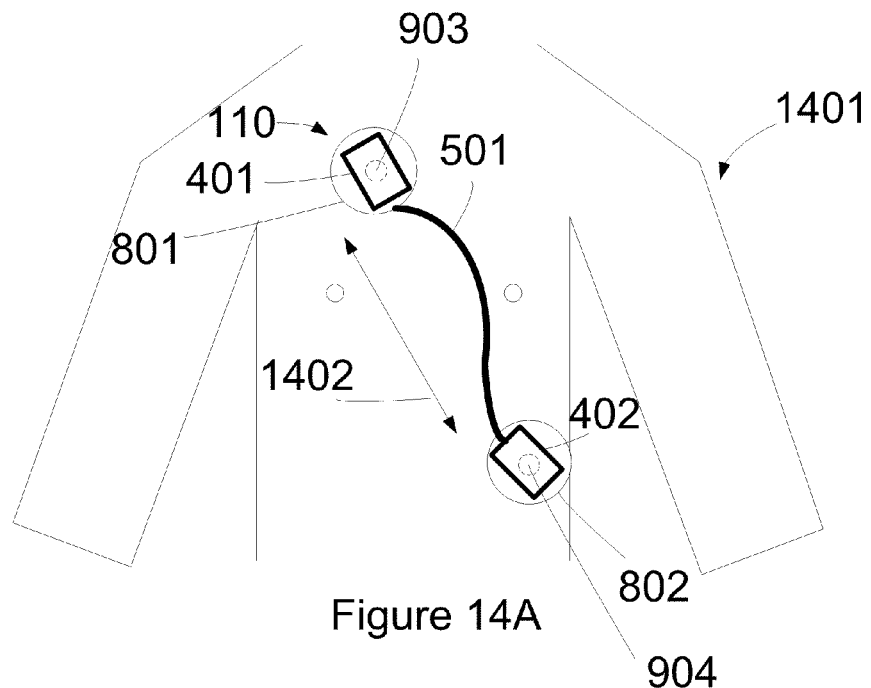
FIG. 14A is an illustration of a retractable multi-use cardiac monitor attached to a cardiac monitoring patient, according to one embodiment.

FIG. 14A is an illustration of a retractable multi-use cardiac monitor 110 attached to a cardiac monitoring patient 1401, according to one embodiment. The multi-use cardiac monitor 110 is configured to collect ECG signals through the left 801 and right 802 wearable electrodes that are connected to the patient's 1401 skin. FIG. 14A illustrates a distance 1402 between the left 401 and right 402 sides of the retractable multi-use cardiac monitor 110. As discussed above with respect to FIG. 5, the retractable multi-use cardiac monitor 110 is configured to allow the left 401 and right 402 sides to be extended away from and toward one another. As discussed above with respect to FIG. 5, the retractable nature of the wire 501 also allows for easy storage of the wire 501.

Furthermore the retractable wire 501 allows the distance 1402 between the left 401 and right 402 sides of the retractable multi-use cardiac monitor 110 to be variable. The variable nature of the distance 1402 between the left 401 and right 402 sides allows a user of the retractable multi-use cardiac monitor 110 to adjust the distance between the left 801 and right 802 wearable contact electrodes that are connected to the patient's 1401 skin and are used to collect ECG signals. Similarly, the variable nature of the distance 1402 allows a user to adjust the vector length between the corresponding left 903 and right 904 sensing connectors to which the left 801 and right 802 wearable contact electrodes are attached. The distance 1402 can be adjusted by the patient 1401 to achieve an optimum electrode vector length between the left 903 and right 904 sensing connectors for ECG signal collection. In some embodiments, the retractable multi-use cardiac monitor 110 alone or in combination with another cardiac monitor is configured to assist the patient 1401 with the determination of an optimum electrode vector length.

Interelectrode distance (vector length) significantly affects the strength and fidelity of detected ECG signals. Various studies have been conducted that analyze the effect of interelectrode distance (vector length) on collected ECG signals. M. Puurtinen, et al., "Estimation of ECG Signal of closely separated bipolar electrodes using thorax models," Proceedings of the 26th Annual International Conference of the IEEE EMBS pp. 801-804, San Francisco, Calif., USA, Sep. 1-5, 2004 which is herein incorporated by reference in its entirety.

Figures 14B, 14C, 14D, 14E:
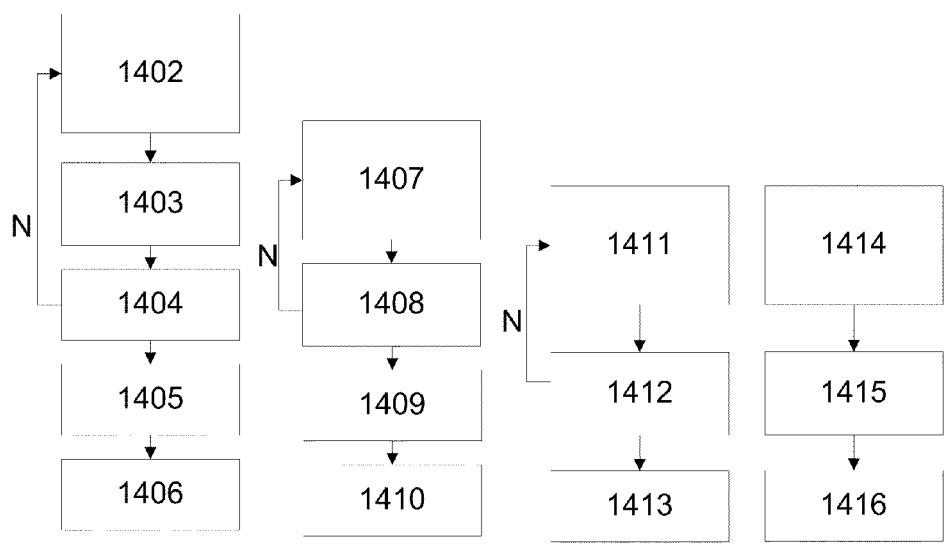
FIG. 14B is a flowchart illustrating the determination of an optimum electrode vector length, according to one embodiment.
FIG. 14C is a flowchart illustrating the determination of an optimum electrode vector length, according to one embodiment.
FIG. 14D is a flowchart illustrating the determination of an optimum electrode vector length, according to one embodiment.
FIG. 14E is a flowchart illustrating the collection and transmission of data, according to one embodiment.

FIG. 14B is a flowchart illustrating the determination of an optimum electrode vector length, according to one embodiment. The FIG. 14B flowchart illustrates the steps of optimum electrode vector length determination from the perspective of a cardiac monitor (e.g. base unit 105 of FIG. 1 or smart phone of FIG. 3A), in an embodiment where a retractable multi-use cardiac monitor 110 is used with another cardiac monitor to determine the optimum electrode vector length between the left 903 and right 904 sensing connectors. In step 1402, data is received by the cardiac monitor (e.g. base unit 105 of FIG. 1 or smart phone of FIG. 3A) from the retractable multi-use cardiac monitor 110 representing a distance between the left 401 and right 402 sides of the retractable multi-use cardiac monitor 110 (and consequently left 903 and right 904 sensing connectors). In step 1403, ECG data collected by the retractable multi-use cardiac monitor 110 at the current distance between the left 401 and right 402 sides is received by the cardiac monitor (e.g. base unit 105 of FIG. 1 or smart phone of FIG. 3A). In step 1404, the received ECG collected data and the data representing the distance between the left 401 and right 402 sides are recorded by the cardiac monitor (e.g. base unit 105 of FIG. 1 or smart phone of FIG. 3A). The received ECG collected data and the data representing the distance between the left 401 and right 402 may be recoded in a memory. Steps 1402 through 1404 are repeated a number of times N with various distances between the left 401 and right 402 sides of the retractable multi-use cardiac monitor 110. In some embodiments, the number of times N is variable. In other embodiments, the number of times N is constant. In yet other embodiments, the number of times N is variable and depends on intermediate calculations performed from the collected ECG data and distance values. In step 1405, an optimum electrode vector length between the left 903 and right 904 sensing connectors is calculated based on the ECG and distance data recorded in step 1404 by the processor of the cardiac monitor (e.g. by the processor of base unit 105 of FIG. 1 or the processor of smart phone 301 of FIG. 3A). In step 1406, a notification is generated indicating the optimum electrode vector length has been found. The notification may be generated by the cardiac monitor (e.g. base unit 105 of FIG. 1 or smart phone of FIG. 3A) or the retractable multi-use cardiac monitor 110. In some embodiments, the notification is an audible noise. In other embodiments, the notification is visual such as by a light or a display on a visual display (e.g. 2101 of FIG. 21 or 2201 of FIG. 22) of the retractable multi-use cardiac monitor 110, or by a light or a visual display on the display of a cardiac monitor (e.g. on a display 175 of base unit 105 of FIG. 1 or a display 305 of smart phone 301 of FIG. 3A).

In one embodiment, an optimum electrode vector length is calculated based on comparison of recorded signal strengths of ECG data at various vector distances collected by Steps 1402 through 1404. In another embodiment, an optimum electrode vector length is calculated based on comparison of recorded signal fidelities of ECG data at various vector distances collected by Steps 1402 through 1404. In another embodiment, an optimum electrode vector length is calculated based on comparison of both recorded signal strengths as well as recorded signal fidelities of ECG data at various vector distances collected by Steps 1402 through 1404. In yet other embodiments, an optimum electrode vector length is calculated based on analyzing the ECG data at various vector distances collected by Steps 1402 through 1404 to determine if the collected ECG data represents a high fidelity QRS ECG pattern. In yet other embodiments, other signal quality measures are used to calculate an optimum vector length. The intermediate calculations noted above in reference to FIG. 14B may be any of these operations.

FIG. 14C is a flowchart illustrating the determination of an optimum electrode vector length, according to one embodiment. The FIG. 14C flowchart illustrates the steps of optimum electrode vector length determination from the perspective of a retractable multi-use cardiac monitor 110 in an embodiment where the retractable multi-use cardiac monitor 110 determines the optimum vector electrode between the left 903 and right 904 sensing connectors by itself. In step 1407, the retractable multi-use cardiac monitor 110 determines a distance between the left 401 and right 402 sides (and consequently left 903 and right 904 sensing connectors) of the retractable multi-use cardiac monitor 110 and the retractable multi-use cardiac monitor 110 records the distance. In step 1408, the retractable multi-use cardiac monitor 110 collects and records ECG data. The ECG data and distance between the left 401 and right 402 sides may be recorded in a memory of the retractable multi-use cardiac monitor 110. Steps 1407 and 1408 are repeated a number of times N with various distances between the left 401 and right 402 sides. In some embodiments, the number of times N is variable. In other embodiments, the number of times N is constant. In yet other embodiments, the number of times N is variable and depends on intermediate calculations performed from the collected ECG data and distance between the left 401 and right 402 sides. In step 1409, an optimum electrode vector length between the left 903 and right 904 sensing connectors is calculated based on the ECG data at various vector distances recorded in steps 1407 and 1408 by a processor of the retractable multi-use cardiac monitor 110. In step 1410, the retractable multi-use cardiac monitor 110 generates a notification indicating the optimum electrode vector length has been found. In some embodiments, the notification is an audible noise. In other embodiments, the notification is visual such as by a light or a display on a display screen (e.g. 2101 of FIG. 21 or 2201 of FIG. 22) of the retractable multi-use cardiac monitor 110.

In one embodiment, an optimum electrode vector length is calculated based on comparison of recorded signal strengths of ECG data at various vector distances collected by Steps 1407 and 1408. In another embodiment, an optimum electrode vector length is calculated based on comparison of recorded signal fidelities of ECG data at various vector distances collected by Steps 1407 and 1408. In another embodiment, an optimum electrode vector length is calculated based on comparison of both recorded signal strengths as well as recorded signal fidelities of ECG data at various vector distances collected by Steps 1407 and 1408. In yet other embodiments, an optimum electrode vector length is calculated based on analyzing the ECG data at various vector distances collected by Steps 1407 and 1408 to determine if the collected ECG data represents a high fidelity QRS ECG pattern. In yet other embodiments, other signal quality measures are used to calculate an optimum vector length. The intermediate calculations noted above in reference to FIG. 14C may be any of these operations.

FIG. 14D is a flowchart illustrating the determination of an optimum electrode vector length, according to one embodiment. The FIG. 14D flowchart illustrates the steps of optimum electrode vector length determination from the perspective of a patient or a healthcare professional. In FIG. 14D, the retractable multi-use cardiac monitor 110 alone or in combination with another cardiac monitor is configured to assist the patient or healthcare professional with the determination of an optimum electrode vector length as explained in FIGS. 14B and 14C above. In step 1411, the patient or healthcare professional adjusts a distance between the left 401 and right 402 sides of the retractable multi-use cardiac monitor 110. In step 1412, the patient or healthcare professional holds the retractable multi-use cardiac monitor 110 against a portion of a patient body to record data. Steps 1411 and 1412 are repeated a number of times N with various distances between the left 401 and right 402 sides. In some embodiments, the number of times N is variable. In other embodiments, the number of times N is constant. In yet other embodiments, the number of times N is variable and depends on intermediate calculations performed from the collected data and distance adjustments. In step 1413, the patient or healthcare professional receives a notification of the optimum electrode vector length from either a cardiac monitor (e.g. base unit 105 of FIG. 1 or smart phone 301 of FIG. 3A) or from the retractable multi-use cardiac monitor 110, as explained above in the discussion of FIGS. 14B and 14C. In an alternative embodiment, the patient or healthcare professional does not receive a notification in step 1413. Rather, the patient or healthcare professional reviews the iteratively collected ECG data at various vector distances to determine the optimum vector length. For example, the patient or healthcare professional could review such data on a display screen (e.g. 2101 of FIG. 21 or 2201 of FIG. 22) of the retractable multi-use cardiac monitor 110, or on a display screen of a cardiac monitor (e.g. display 175 of base unit 105 of FIG. 1 or display 305 of smart phone 301 of FIG. 3A).

FIG. 14E is a flowchart illustrating the collection of and transmission of data, according to one embodiment. In step 1414, the retractable multi-use cardiac monitor 110 collects ECG or other biological data as described above. In some embodiments, ECG or biological data may be collected from more than two electrodes or sensing connectors as described, for example, in reference to FIGS. 17, 19, and 20 below. In step 1415, the collected data is stored. The collected data may be stored in a memory of the retractable multi-use cardiac monitor 110. The collected data is then transmitted as described in the various embodiments above to a destination.

Figure 15:
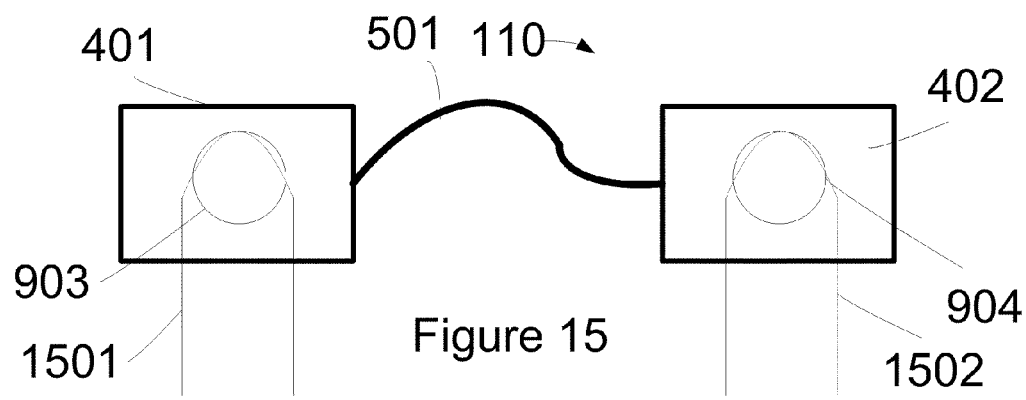
FIG. 15 is an illustration of a finger electrode configuration of a retractable multi-use cardiac monitor, according to one embodiment.
Figure 16:
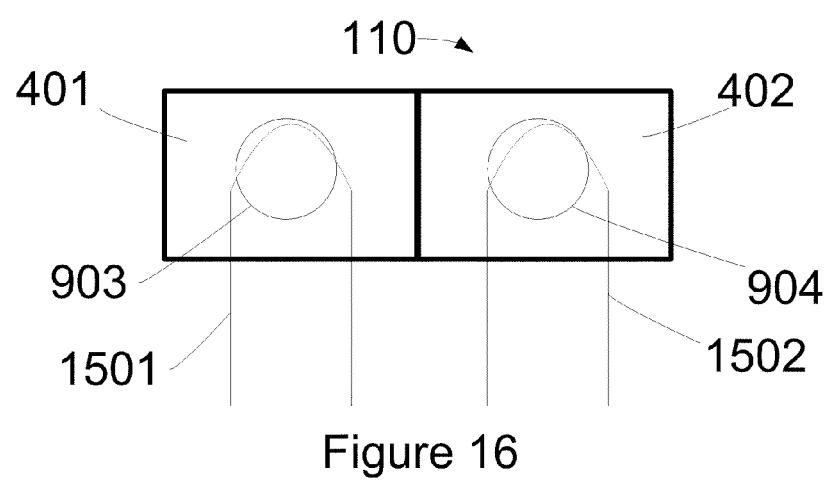
FIG. 16 is an illustration of a finger electrode configuration of a retractable multi-use cardiac monitor, according to one embodiment.

FIG. 15 is an illustration of a finger electrode configuration of the retractable multi-use cardiac monitor 110, according to one embodiment. In the illustrated embodiment, a user of the retractable multi-use cardiac monitor 110 is placing a left side finger 1501 and a right side finger 1502 onto the left 903 and right 904 sensing connectors respectively. In the illustrated embodiment, the left 1501 and right 1502 fingers are from different hands. The retractable multi-use cardiac monitor 110 as illustrated in FIG. 15 may collect ECG data from a patient when that patient applies the left 1501 and right 1502 side fingers onto the left 903 and right 904 sensing connectors, respectively. FIG. 16 is also an illustration of a finger electrode configuration of the retractable multi-use cardiac monitor 110 with the wire 501 retracted. The FIG. 16 embodiment illustrates a left 1501 and right 1502 finger attached to the left 903 and right 904 sensing connectors respectively. In the illustrated embodiments of FIGS. 15 and 16, the left 903 and right 904 sensing connectors may be contacted to any body part of a patient to collect ECG data. For example, left 903 and right 904 sensing connectors can be contacted to the chest, the legs, ankles, wrists or the arms of a patient. Further, the left 903 and right 904 sensing connectors may be designed with different shapes or sizes. In some embodiments, the left 903 and right 904 sensing connectors are shaped to receive a finger. As an example, a patient may not be feeling well, and may desire to make a short recording of ECG data without attaching wearable electrodes by merely holding the left 903 and right 904 sensing connectors against their chest for a short period. As a further example, a patient may desire to temporarily hold the left 903 and right 904 sensing connectors against their chest by moving the left 401 and right 402 sides of the retractable multi-use cardiac monitor 110 away from one another to create an optimum vector length as illustrated in FIG. 14A.

Figure 17:
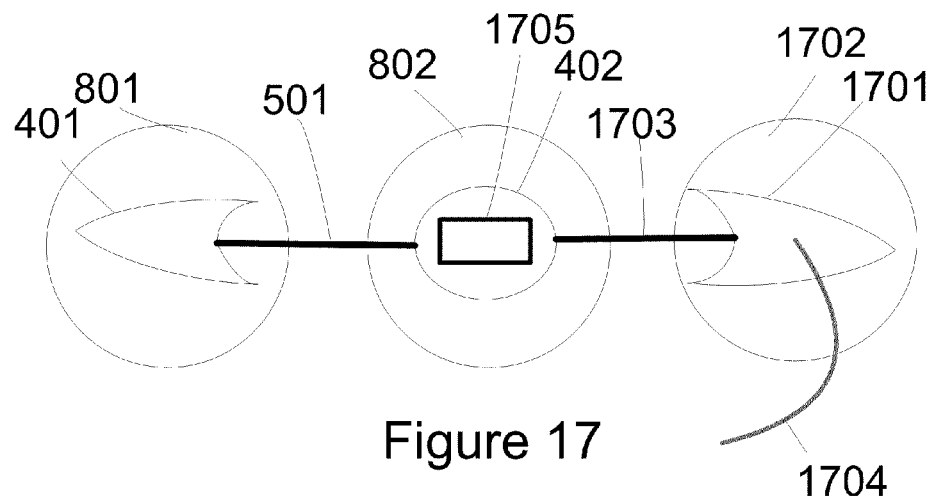
FIG. 17 is a top-down view of a retractable multi-use cardiac monitor that includes multiple additional wires, according to one embodiment.

FIG. 17 is a top-down view of a retractable multi-use cardiac monitor 110 that includes a second retractable wire 1703, according to another embodiment. In the illustrated embodiment, the retractable multi-use cardiac monitor 110 includes a second wire 1703 connected to a third portion 1701 of the retractable multi-use cardiac monitor 110. The third portion 1701 is also attached to a third 1702 wearable electrode and is comprised of a third housing (also referenced as 1701). The third wearable electrode 1702 may be connected to a patient's skin along with the left 801 and right 802 side wearable electrodes, thereby providing an increased number of electrode contacts on the patient's skin and increasing the quality of the collected ECG signal. In an alternative embodiment, the third wearable electrode 1702 is used as a ground. In one embodiment, the second wire 1703 retracts into the right side 402. In an alternative embodiment, the second wire 1703 retracts into the third portion 1701. In one embodiment, the second wire 1703 is detachable from the third portion 1701. In an alternative embodiment, the second wire 1703 simply plugs into a portion of the right side 402. In further embodiments, there may be an unlimited number of retractable or connectable wires which may retract or connect to either the left 401 or right sides 402 for use in the collection of electrical signals from a patient's heart, for reference wires, or electrical grounds. For example, FIG. 17 also illustrates a simple wire 1704 that is connected to the top of the right 402 side of the retractable multi-use cardiac monitor 110. Wire 1704 may be a ground or a signal wire.

FIG. 17 also illustrates a symptom button 1705. The symptom button 1705 may operate as described above with respect to FIG. 4. Additionally, the symptom button may be used when a patient desires to collect a short amount of data by temporarily placing the retractable multi-use cardiac monitor 110 against the patient's body, or if the patient desires to collect data using the sensing connectors 903 and 904 as finger electrodes as discussed in FIGS. 15 and 16. In such an embodiment, only two of the left 401 and right 402 sides or the third portion 1701 should be active for the collection of ECG data. In such an embodiment, the symptom button 1705 or a dip switch or other means may be used to indicate to the monitor that only 2 of 3 electrodes will be used. For example, the symptom button 1705 or a dip switch or other means could be used to disable the right 402 side, leaving only the left side 401 and the third portion 1701 active for the collection of ECG data during temporary placement of the retractable multi-use cardiac monitor 110 against a portion of a patient body. The non-designation of the right side 402 during data collection eliminates any electrical noise that may be provided by the right side 402 during collection and allows for electrical isolation of the left side 401 and right portion 1701 relative to one another.

Figure 18:
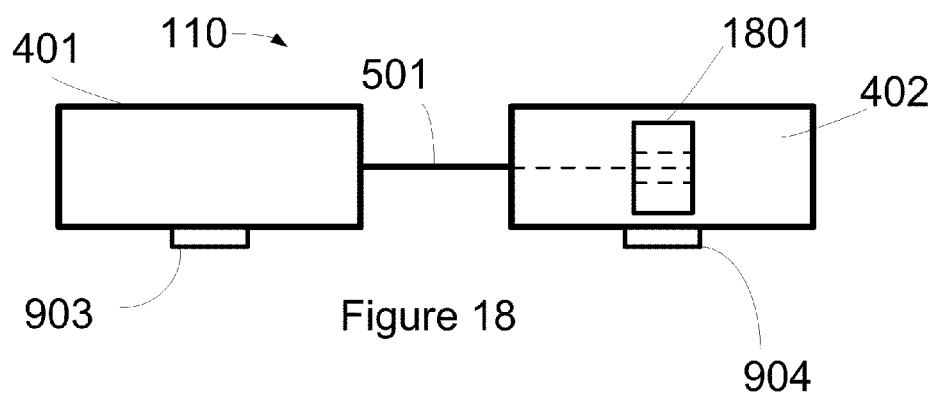
FIG. 18 is a side-view of a retractable multi-use cardiac monitor, according to one embodiment.
Figure 19:
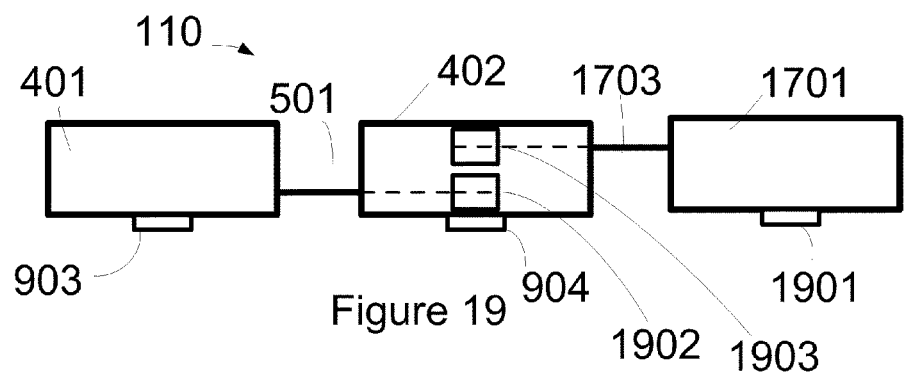
FIG. 19 is a side-view of a retractable multi-use cardiac monitor, according to one embodiment.
Figure 20:
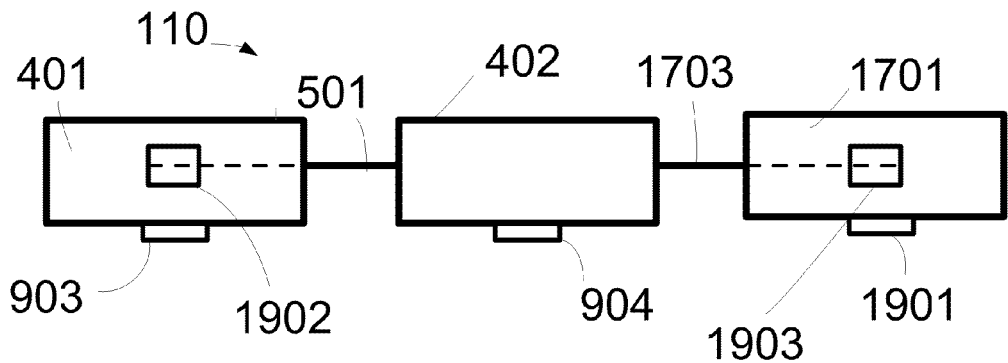
FIG. 20 is a side-vide of a retractable multi-use cardiac monitor, according to one embodiment.

FIG. 18 is a side-view of a retractable multi-use cardiac monitor, according to one embodiment. FIG. 18 illustrates an embodiment where the wire 501 retracts into the right 402 side of the retractable multi-use cardiac monitor 110 using a single wire retraction barrel 1801 as a wire retractor. As discussed above, the wire 501 may retract into the left 401 side of the retractable multi-use cardiac monitor 110, and in such an embodiment the left 401 side would include a single wire retraction barrel as a wire refractor. FIG. 19 is also a side-view of a retractable multi-use cardiac monitor, according to one embodiment. The embodiment illustrated in FIG. 19 includes left 401 and right 402 sides as well as a third portion 1701. The illustrated embodiment also includes a wire 501 and a second wire 1703. The wire 501 and second wire 1703 retract into the right side 402 by a first 1902 and second 1903 retraction barrel respectively as wire retractors. The FIG. 19 embodiment also illustrates a third sensing connector 1901. FIG. 20 is a further illustration of a side-view of a retractable multi-use cardiac monitor 110, according to one embodiment. In the FIG. 20 embodiment, the first refraction barrel 1902 is within the left side 401 and the second retraction barrel 1903 is within the third portion 1701. In the illustrated embodiment, the wire 501 retracts into the left side 401 by the first retraction barrel 1902, and the second wire 1703 retracts into the third portion 1701 by the second retraction barrel 1903.

Figure 21:
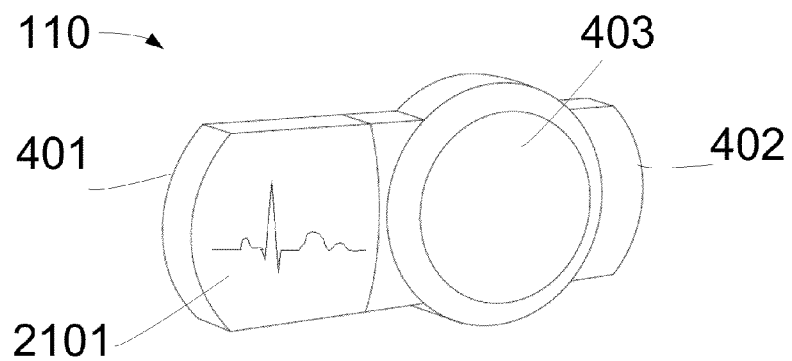
FIG. 21 is a top-down view of a retractable multi-use cardiac monitor, according to one embodiment.
Figure 22:
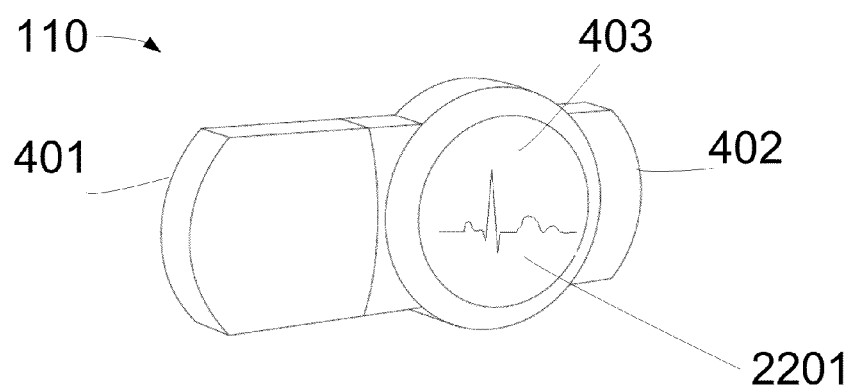
FIG. 22 is a top-down view of a retractable multi-use cardiac monitor, according to one embodiment.

FIG. 21 is yet another illustration of an embodiment of a retractable multi-use cardiac monitor 110. The illustrated embodiment includes left 401 and right 402 sides. The illustrated embodiment also includes a display screen 2101 which is configured to display captured ECG or other biological data. FIG. 22 similarly illustrates an embodiment of a retractable multi-use cardiac monitor 110, where a display screen 2201 is provided on the right side 402 in conjunction with the symptom button 403.

Figure 23A:
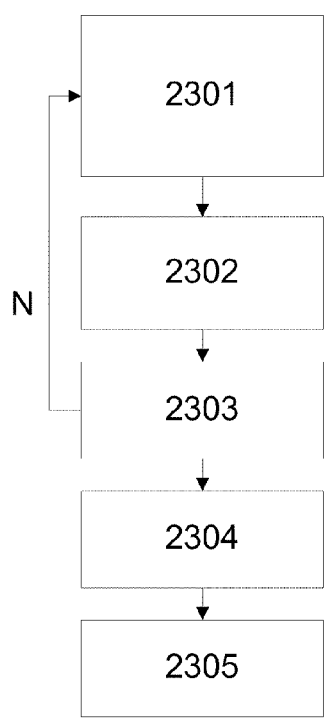
FIG. 23A is a flowchart illustrating the determination of a set of optimum electrode vector lengths, according to one embodiment.

FIG. 23A is a flowchart illustrating the determination of an optimum set of electrode vector lengths, according to one embodiment. The embodiment of FIG. 23A is directed to the determination of an optimum set of electrode vector lengths with an embodiment of the retractable multi-use cardiac monitor 110 that includes both left 401 and right sides 402, as well as a third portion 14071 as illustrated, for example, in FIGS. 17, 19, and 20 and discussed above. The FIG. 23A flowchart illustrates the steps of optimum electrode vector length determination from the perspective of a cardiac monitor (e.g. base unit 105 of FIG. 1 or smart phone of FIG. 3A), in an embodiment where a retractable multi-use cardiac monitor 110 is used with another cardiac monitor to determine the optimum electrode vector length between the left 903 and right 904 sensing connectors, as well as the optimum electrode vector length between the right sensing connector 904 and the third sensing connector 1901. In step 2301, data is received by the cardiac monitor (e.g. base unit 105 of FIG. 1 or smart phone of FIG. 3A) from the retractable multi-use cardiac monitor 110 representing a distance between the left 401 and right 402 sides of the retractable multi-use cardiac monitor 110 (and consequently left 903 and right 904 sensing connectors), as well as data representing a distance between the right side 402 and the third portion 1701 of the retractable multi-use cardiac monitor 110 (and consequently the right sensing connector 904 and the third sensing connector 1901). In some embodiments, if any of the left 401 side, right 402 side, or third portion 1701 have not moved since a previous iteration, a determination may be made by not sensing any such movement. In step 2302, ECG data collected by the retractable multi-use cardiac monitor 110 at the current distances between the left side 401, right side 402, and third portion 1701, respectively, is received by the cardiac monitor (e.g. base unit 105 of FIG. 1 or smart phone of FIG. 3A). In step 2303, the received ECG collected data and the data representing the distance between the left 401 and right 402 sides, and the distance between the right side 402 and the third portion 1701 are recorded by the cardiac monitor (e.g. base unit 105 of FIG. 1 or smart phone of FIG. 3A). The received ECG collected data and the data representing the distances between the left side 401, right side 402, and third portion 1701, respectively, may be recoded in a memory. Steps 2301 through 2303 are repeated a number of times N with various distances between the left side 401, right side 402, and third portion 1701, respectively of the retractable multi-use cardiac monitor 110. In some embodiments, the number of times N is variable. In other embodiments, the number of times N is constant. In yet other embodiments, the number of times N is variable and depends on intermediate calculations performed from the collected ECG data and distance values. In step 2304, a set of optimum electrode vector lengths between the left side 401, right side 402, and third portion 1701, respectively, is calculated based on the ECG and distance data recorded in Step 2303 by the processor of the cardiac monitor (e.g. by the processor of base unit 105 of FIG. 1 or the processor of smart phone 301 of FIG. 3A). In step 2305, a notification is generated indicating the optimum set of electrode vector lengths has been found. The notification may be generated by the cardiac monitor (e.g. base unit 105 of FIG. 1 or smart phone of FIG. 3A) or the retractable multi-use cardiac monitor 110. In some embodiments, the notification is an audible noise. In other embodiments, the notification is visual such as by a light or a display on a visual display (e.g. 2101 of FIG. 21 or 2201 of FIG. 22) of the retractable multi-use cardiac monitor 110, or by a light or a visual display on the display of a cardiac monitor (e.g. on a display 175 of base unit 105 of FIG. 1 or a display 305 of smart phone 301 of FIG. 3A).

In one embodiment, a set of optimum vector lengths is calculated based on comparison of recorded signal strengths of ECG data at various vector distances collected by Steps 2301 through 2303. In another embodiment, a set of optimum vector lengths is calculated based on comparison of recorded signal fidelities of ECG data at various vector distances collected by Steps 2301 through 2303. In another embodiment, a set of optimum vector lengths is calculated based on comparison of both recorded signal strengths as well as recorded signal fidelities of ECG data at various vector distances collected by Steps 2301 through 2303. In yet other embodiments, a set of optimum vector lengths is calculated based on analyzing the ECG data at various vector distances collected by Steps 2301 through 2303 to determine if the collected ECG data represents a high fidelity QRS ECG pattern. In yet other embodiments, other signal quality measures are used to calculate an optimum vector lengths. The intermediate calculations noted above in reference to FIG. 23A may be any of these operations.

Figure 23B:
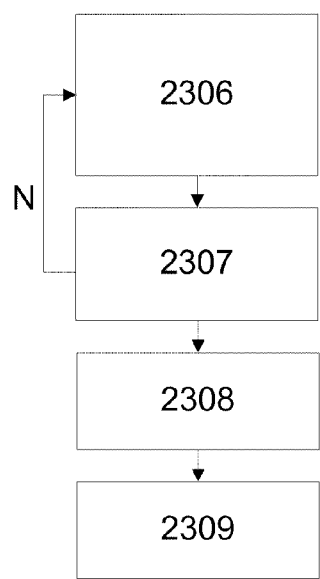
FIG. 23B is a flowchart illustrating the determination of a set of optimum electrode vector lengths, according to one embodiment.

FIG. 23B is a flowchart illustrating the determination of an optimum set of electrode vector lengths, according to one embodiment. The FIG. 23B flowchart illustrates the steps of optimum electrode vector length determination from the perspective of a retractable multi-use cardiac monitor 110 in an embodiment where the retractable multi-use cardiac monitor 110 determines an optimum set of electrode vector lengths by itself. Further, the FIG. 23B flowchart is directed to the determination of an optimum set of electrode vector lengths in an embodiment of the retractable multi-use cardiac monitor 110 that includes both left 401 and right sides 402, as well as a third portion 1701 as illustrated, for example, in FIGS. 17, 19, and 20 and discussed above. In step 2306, the retractable multi-use cardiac monitor 110 determines a distance between the left 401 and right 402 sides of the retractable multi-use cardiac monitor 110 (and consequently left 903 and right 904 sensing connectors), and distance between the right side 402 and the third portion 1701 of the retractable multi-use cardiac monitor 110 (and consequently the right sensing connector 904 and the third sensing connector 1901). In some embodiments, if any of the left 401, right 402, or third portion 1701 have not moved since a previous iteration, a determination may be made by not sensing any such movement. Data representing each of the distances is recorded. In step 2307, the retractable multi-use cardiac monitor 110 collects and records ECG data using each of the left 903, right 904, and third 1901 sensing connectors. The ECG data collected and the distances between the left side 401, right side 402, and third portion 1701, respectively, may be recorded in a memory of the retractable multi-use cardiac monitor 110. Steps 2306 and 2307 are repeated a number of times N with various distances between the left side 401, right side 402, and third portion 1701, respectively. In some embodiments, the number of times N is variable. In other embodiments, the number of times N is constant. In yet other embodiments, the number of times N is variable and depends on intermediate calculations performed from the collected ECG data and distances between the left side 401, right side 402, and third portion 1701, respectively. In step 2308, a set of optimum electrode vector lengths between the left side 401, right side 402, and third portion 1701, respectively, is calculated based on the ECG and distance data collected in Steps 2306 and 2307 by a processor of the retractable multi-use cardiac monitor 110. In step 2309, a notification is generated indicating the optimum set of electrode vector lengths has been found. In some embodiments, the notification is an audible noise. In other embodiments, the notification is visual such as by a light or a display on a display screen (e.g. 2101 of FIG. 21 or 2201 of FIG. 22) of the retractable multi-use cardiac monitor 110.

In one embodiment, a set of optimum vector lengths is calculated based on comparison of recorded signal strengths of ECG data at various vector distances collected by Steps 2306 and 2307. In another embodiment, a set of optimum vector lengths is calculated based on comparison of recorded signal fidelities of ECG data at various vector distances collected by Steps 2306 and 2307. In another embodiment, a set of optimum vector lengths is calculated based on comparison of both recorded signal strengths as well as recorded signal fidelities of ECG data at various vector distances collected by Steps 2306 and 2307. In yet other embodiments, a set of optimum vector lengths is calculated based on analyzing the ECG data at various vector distances collected by Steps 2306 and 2307 to determine if the collected ECG data represents a high fidelity QRS ECG pattern. In yet other embodiments, other signal quality measures are used to calculate an optimum vector length. The intermediate calculations noted above in reference to FIG. 23B may be any of these operations.

Figure 23C:
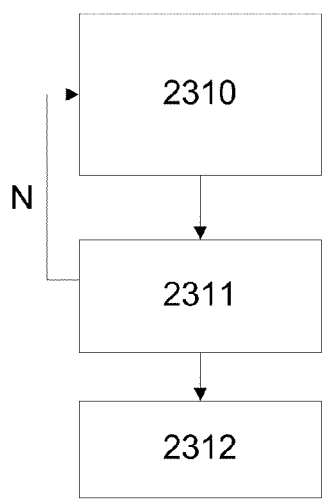
FIG. 23C is a flowchart illustrating the determination of a set of optimum electrode vector lengths, according to one embodiment.

FIG. 23C is a flowchart illustrating the determination of a set of optimum electrode vector lengths, according to one embodiment. The FIG. 23C flowchart illustrates the steps of optimum electrode vector length determination from the perspective of a patient or a healthcare professional. In FIG. 23C, the retractable multi-use cardiac monitor 110 alone or in combination with another cardiac monitor is configured to assist the patient or healthcare professional with the determination of a set of optimum electrode vector lengths as explained in FIGS. 23A and 23B above. The embodiment of FIG. 23C is directed to the determination of an optimum set of electrode vector lengths with an embodiment of the retractable multi-use cardiac monitor 110 that includes both left 401 and right sides 402, as well as a third portion 14071 as illustrated, for example, in FIGS. 17, 19, and 20 and discussed above. In step 2310, the patient or healthcare professional adjusts at least one of a distance between the left 401 and right 402 sides of the retractable multi-use cardiac monitor 110, or a distance between the right side 402 and the third portion 1701. In step 2310, the patient or healthcare professional may adjust both distances. In step 2311, the patient or healthcare professional holds or applies the retractable multi-use cardiac monitor 110 against a portion of a patient body to record data. Steps 2311 and 2312 are repeated a number of times N with various distances between the left side 401, right side 402, and third portion 1701, respectively. In some embodiments, the number of times N is variable. In other embodiments, the number of times N is constant. In yet other embodiments, the number of times N is variable and depends on intermediate calculations performed from the collected data and distance adjustments. In step 2312, the patient or healthcare professional receives a notification indicating that the set of optimum electrode vector lengths has been found from either a cardiac monitor (e.g. base unit 105 of FIG. 1 or smart phone 301 of FIG. 3A) or from the retractable multi-use cardiac monitor 110, as explained above in the discussion of FIGS. 23A and 23B. In an alternative embodiment, the patient or healthcare professional does not receive a notification in step 2312. Rather, the patient or healthcare professional reviews the iteratively collected ECG data at various vector distances to determine the set of optimum vector lengths. For example, the patient or healthcare professional could review such data on a display screen (e.g. 2101 of FIG. 21 or 2201 of FIG. 22) of the retractable multi-use cardiac monitor 110, on a display screen of a cardiac monitor (e.g. display 175 of base unit 105 of FIG. 1 or display 305 of smart phone 301 of FIG. 3A).

One of skill in the art would recognize that the methods of determining a set of optimum vector lengths as disclosed above in reference to FIGS. 23A, 23B, and 23C are similarly applicable to a retractable multi-use cardiac monitor 110 with any number of portions or sides that include sensing connectors or electrodes, or any number of wires that are connected to sensing connectors or electrodes.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

What is claimed is:

1. A method of determining an optimum electrode vector length between a first sensing connector of a first side of a retractable multi-use cardiac monitor and a second sensing connector of a second side of the retractable multi-use cardiac monitor, comprising:
    (A) receiving from the retractable multi-use cardiac monitor at a smart phone data representing a distance between the first sensing connector of the retractable multi-use cardiac data monitor and the second sensing connector of the retractable multi-use cardiac data monitor, wherein the smart phone includes a processor;
    (B) receiving electrocardiogram (ECG) data collected by the retractable multi-use cardiac data monitor through the first and second sensing connectors;
    (C) recording the ECG data collected in step B and the data representing the distance between the first and second sensing connectors received in step A;
    (D) iteratively repeating steps A-C a number of times;
    (E) calculating, by the processor of the smart phone, an optimum electrode vector length between the first sensing connector of the first side of the retractable multi-use cardiac monitor and the second sensing connector of the second side of the retractable multi-use cardiac monitor based on the ECG data collected in step B and the data representing the distance between the first and second sensing connectors received in step A;
    (F) generating a notification of that the optimum electrode vector length has been found.

2. A method of determining an optimum electrode vector length between a first sensing connector of a first side of a retractable multi-use cardiac monitor and a second sensing connector of a second side of the retractable multi-use cardiac monitor, comprising:
    (A) determining a distance between the first sensing connector of the retractable multi-use cardiac data monitor and the second sensing connector of the retractable multi-use cardiac data monitor, and recording data representing the distance;
    (B) collecting electrocardiogram (ECG) data through the first and second sensing connectors and recording the collected ECG data;
    (C) iteratively repeating A-B a number of times;
    (E) calculating, by a processor of the retractable multi-use cardiac monitor an optimum electrode vector length between the first sensing connector of the first side of the retractable multi-use cardiac monitor and the second sensing connector of the second side of the retractable multi-use cardiac monitor based on the ECG data collected in step B and the data representing the distance between the first and second sensing connectors recorded in step A;
    (F) generating a notification of that the optimum electrode vector length has been found.

* * * * *